United States Patent [19] [11] 4,237,326
Fuga et al. [45] Dec. 2, 1980

[54] METHOD OF INHIBITING POLYMERIZATION OF STYRENE

[75] Inventors: Nobuhiko Fuga, Tateno; Kunio Uchimura, Ami; Hideyuki Takahashi, Yokkaichi, all of Japan

[73] Assignee: Mitsubishi Petrochemical Company Limited, Tokyo, Japan

[21] Appl. No.: 43,661

[22] Filed: May 30, 1979

[51] Int. Cl.³ .................. B01D 3/34; C10G 9/16; C07C 7/20; C07C 15/46
[52] U.S. Cl. .................................. 585/4; 203/9; 203/50; 203/51; 203/57; 203/62; 208/48 AA; 585/952
[58] Field of Search ............... 585/4, 5, 952; 208/48 AA; 203/9, 62, 50, 51, 57; 260/396 N, 396 R

[56] References Cited

U.S. PATENT DOCUMENTS

| | | | |
|---|---|---|---|
| 2,446,969 | 8/1948 | Welch et al. | 203/9 X |
| 3,527,822 | 9/1970 | Benson | 203/9 |
| 3,775,493 | 11/1973 | DeSimone et al. | 585/3 |
| 3,787,515 | 1/1974 | Gorbunov et al. | 203/9 |
| 3,816,267 | 6/1974 | Chuang | 203/8 |
| 4,061,545 | 12/1977 | Watson | 203/9 |
| 4,132,603 | 1/1979 | Watson | 203/9 |

Primary Examiner—Delbert E. Gantz
Assistant Examiner—G. E. Schmitkons
Attorney, Agent, or Firm—Oblon, Fisher, Spivak, McClelland & Maier

[57] ABSTRACT

A method of inhibiting the polymerization of styrene which comprises mixing with the styrene a minor but effective quantity of an inhibitor compound selected from the group consisting of 2-methylbenzoquinone-4-oxime, 2,3,5-trimethylbenzoquinone-4-oxime and mixtures thereof.

6 Claims, No Drawings

METHOD OF INHIBITING POLYMERIZATION OF STYRENE

BACKGROUND OF THE INVENTION

The present invention relates to a method of inhibiting the polymerization of styrene at high temperatures. More particularly, the present invention relates to a method of inhibiting the polymerization of styrene which comprises using a methyl-substituted benzoquinone-4-oxime as a polymerization inhibitor.

A large number of compounds have been hitherto studied as a polymerization inhibitor for styrene. However, because the polymerization behavior of styrene at high temperatures is remarkably different from that at low temperatures, a polymerization inhibitor which is useful at low temperatures often exhibits almost no inhibitory activity at high temperatures, for example, in a temperature range (of about 80° to 130° C.) which is encountered during the distillation of styrene. Furthermore, conventional polymerization inhibitors are generally useful in the presence of dissolved oxygen. However, dissolved oxygen is present in a very small quantity in a distillation columm used during the production of styrene. Accordingly, most of the conventional polymerization inhibitors lose their capability of inhibiting polymerization under such a condition. For example, t-butyl catechol, hydroquinonemonomethyl ether or phenothiazine which possesses a high inhibitory capability at a low temperature range exhibits little polymerization inhibiting activity at a high temperature range encountered during the distillation of styrene.

Under these circumstances, in order to inhibit the polymerization of styrene in a distillation column in the final refining distillation step of a process for producing styrene from the dehydrogenation of ethylbenzene, sulfur has hitherto been used. However, since the polymerization inhibiting action of sulfur is not always satisfactory, a large amount of distilled residue called styrene bottom is formed. The styrene bottom contains sulfur, and thus, it poses a problem from the air pollution point of view when it is burned for disposal.

The sulfur contained in the styrene bottom can be recovered by washing with an organic solvent for re-use. This necessitates the provision of an additional recovery apparatus. Accordingly, investigations have been directed to the development of a polymerization inhibitor which can serve as a substitute for sulfur without its drawbacks. Thus, various propositions have been made, for example, in Japanese Patent Publication Nos. 86826/73, 75541/74, 72219/74, 124001/74, 81325/74 and 66687/74. However, these conventional polymerization inhibitors have poor inhibiting activity, are sublimable, explosive, thermally unstable, or prone to produce NO, or have low solubility. Accordingly, these inhibitors are not always satisfactory.

In the case of polymerization inhibition in a styrene distillation column, a polymerization inhibitor should have high solubility in addition to high inhibitory activity. A high solubility of a polymerization inhibitor not only greatly contributes to the development of the activity thereof but also makes it possible to feed continuously a constant flow rate of the inhibitor dissolved in styrene or ethylbenzene. In this respect, p-nitrosophenol (British Patent No. 1064845) which is one of the conventional polymerization inhibitors having the highest inhibiting activity is difficult to feed continuously into a practical distillation column at a constant rate because it has remarkably low solubility in styrene and ethylbenzene.

SUMMARY OF THE INVENTION

It is an object of the present invention to overcome the above described difficulties heretofore encountered in the inhibition of polymerization of styrene. It has been found that this object can be achieved by using a particular methylated benzoquinone-4-oxime as a polymerization inhibitor.

More specifically, the polymerization inhibitor for styrene according to the present invention comprises a methylated benzoquinone selected from the group consisting of 2-methylbenzoquinone-4-oxime, 2,3,5-trimethylbenzoquinone-4-oxime and mixtures thereof. It is necessary that benzoquinone-4-monooxime be substituted with a methyl group in the present invention. It is also necessary that a methyl group be present at the 2- or 2,3,5-positions of benzoquinone-4-monooxime (as indicated in Table 1 set forth hereinafter).

Benzoquinone-4-oxime which has undergone this specific substitution has unexpectedly excellent capability of inhibiting the polymerization of styrene at high temperatures (above normal temperature, particularly about 80° to 130° C.) and, at the same time, exhibits high solubility in styrene and ethylbenzene.

DETAILED DESCRIPTION OF THE INVENTION

The methylated benzoquinone-4-oxime of the present invention is represented by the formula

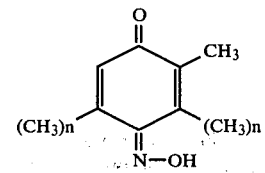

wherein n represents 0 or 1. Benzoquinone monooxime is in tautomerism relation to nitrosophenol, and thus, the above formula may also be set forth as follows.

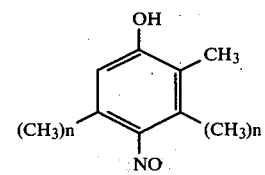

wherein n represents 0 or 1.

The term "2-methyl- or 2,3,5-trimethylbenzoquinone-4-oxime" as used herein includes those oximes at least a portion of which is in the form of tautomers. These oximes may be used in mixtures.

The quantity of the methylated benzoquinone-4-oxime used is at least 0.002% by weight and may be varied depending upon the requirement and usage conditions. Generally, it is in the range of about 0.005 to 0.5, preferably 0.01 to 0.2%, by weight. All percentages are based on the weight of styrene.

The polymerization inhibitor of the present invention may be used at any stage from the production of styrene to the storage thereof. A most advantageous mode of introducing this inhibitor which permits its high capability of inhibiting polymerization at high temperatures and high solubility to be fully exhibited is to feed the inhibitor as a solution thereof in styrene, ethylbenzene or crude styrene into a distillation column used in the production of styrene. The inhibitor may also be introduced in the form of a solution in benzene or toluene. Ordinarily, styrene is produced by the catalytic dehydrogenation of ethyl benzene in vapor phase, and, in this case, styrene is obtained as a mixture with unreacted ethylbenzene. Styrene may also be produced by catalytic dehydration of α-phenethylalcohol. The term "crude styrene" means such a mixture as is the product of the dehydrogenation of ethylbenzene or of the dehydration of α-phenethylalcohol. The mixture is then continuously subjected to distillation to purify and isolate the styrene. The polymerization inhibitor of the present invention is continuously or intermittently fed as a solution thereof in styrene, ethylbenzene or crude styrene, or in benzene or toluene at a concentration such as to introduce the above mentioned quantity into the distillation column (about 80° to 130° C.).

While the polymerization inhibitor of the present invention can exhibit its activity to an ample degree even in the absence of oxygen, it is preferable that it be used in the presence of oxygen.

The nature and utility of the present invention will be indicated more fully by the following examples.

EXAMPLE 1

A 100-ml, three-necked, round-bottom flask was charged with 40 ml of purified styrene monomer (SM) and 250 parts per million (ppm) of 2,3,5-trimethyl-benzoquinone-4-oxime as a polymerization inhibitor. Then, high purity nitrogen was bubbled through the resulting solution for 20 minutes to remove the dissolved oxygen in the styrene. Thereafter, the solution was heated to a temperature of 110° C. and after 2, 4 and 5 hours, the refractive index was determined.

On one hand, the refractive index of a solution of a styrene polymer (having a molecular weight of 2100) dissolved in a styrene monomer was previously measured, and the correlation between the degree of polymerization and the refractive index was determined beforehand. The degree of polymerization was determined by using this correlation. The results were as follows.

|       |         | Degree of polymerization (wt. %) |
|-------|---------|----------------------------------|
| after | 2 hours | 0.0%                             |
|       | 4 hours | 0.0%                             |
|       | 5 hours | 0.5%                             |

EXAMPLE 2 AND COMPARISON EXAMPLE

The procedure described in Example 1 was used to determine the degrees of polymerization of the compounds shown in Table 1. The results are shown in Table 1 together with the results of Example 1.

TABLE 1

|  | Compound | Degree of Polymerization (wt.%) After 2 hours | After 4 hours |
|---|---|---|---|
| Example 1 | 2,3,5-Trimethylbenzoquinone-4-oxime | 0.0 | 0.0 |
| Example 2 | 2-Methylbenzoquinone-4-oxime | 0.0 | 0.0 |
| Comparison Example 1 | None | 14.0 | not less than 20 |
| Example 2 | 2-Ethylbenzoquinone-4-oxime | 0.0 | 4.0 |
| Example 3 | 2,3-Dimethyl-5-isopropylbenzoquinone-4-oxime | 0.0 | 1.0 |
| Example 4 | 2,3-Dimethylbenzoquinone-4-oxime | 0.0 | 1.2 |
| Example 5 | 3,5-Dimethylbenzoquinone-4-oxime | 0.0 | 0.5 |
| Example 6 | 2,6-Dimethylbenzoquinone-4-oxime | 0.5 | 1.5 |
| Example 7 | p-Nitrosophenol | 0.1 | 0.3 |
| Example 8 | 3-Methylbenzoquinone-4-oxime | 1.0 | 10.0 |
| Example 9 | 2,3,6-Trimethylbenzoquinone-4-oxime | 3.0 | 8.5 |
| Example 10 | 2,3,5,6-Tetramethylbenzoquinone-4-oxime | 1.5 | 4.5 |
| Example 11 | 3-Methyl-6-t-butyl-4-nitrosophenol | 1.0 | 2.0 |
| Example 12 | 2,6-Di-t-butylbenzoquinone-4-oxime | 10.0 | not less than 20 |

EXAMPLE 3

2-methylbenzoquinone-4-oxime was added to a styrene-containing reaction liquid having the following composition from a styrene plant dehydrogenation reactor at a rate of 200 ppm by weight of styrene. The resultant liquid was subjected to distillation by using three distillation columns. First, a fraction containing benzene and toluene was separated from a fraction containing ethylbenzene and styrene. Then, ethylbenzene was separated from styrene, and finally, styrene was distilled out over the column. The percent recovery of styrene was 98.2% by weight. The distillation conditions are described hereunder.

Composition of reaction product liquid (by gas chromatography):

|  | % by weight |
|---|---|
| Benzene | 3.1 |
| Toluene | 6.3 |
| Ethylbenzene | 50.0 |
| Styrene | 40.1 |
| Others | 0.5 |
| Distillation conditions: | |
| Inner diameter of distillation column | 3 cm |
| Feed rate of reaction product liquid | 500 cc/hr |
| Temperature at column bottom | 107° C. |
|  | (Number of plates) | (Reflux ratio) |
| Separation of fraction containing benzene and toluene from fraction containing ethylbenzene and styrene | 20 | 7.0 |
| Separation of ethylbenzene from styrene | 70 | 5.5 |

| -continued | | |
|---|---|---|
| Separation of styrene from heavy materials | 20 | 1.0 |

What is claimed is:

1. A method of inhibiting the polymerization of styrene, which comprises: mixing styrene with a minor, but effective proportion of an inhibitor selected from the group consisting of 2-methylbenzoquinone-4-oxime, 2,3,5-trimethylbenzoquinone-4-oxime, and mixtures thereof.

2. The method as claimed in claim 1, wherein said styrene is combined with at least 0.002% by weight of said inhibitor based on styrene.

3. The method as claimed in claim 2, wherein the quantity of said inhibitor ranges from 0.005 to 0.5% by weight based on styrene.

4. A solution of a methylated benzoquinone-4-oxime, which comprises: a methylated benzoquinone selected from the group consisting of 2-methylbenzoquinone-4-oxime, 2,3,5-trimethylbenzoquinone-4-oxime and mixtures thereof dissolved in hydrocarbon solvent selected from the group consisting of styrene or crude styrene and an aromatic hydrocarbon solvent or mixtures thereof.

5. The solution of claim 4, wherein said aromatic hydrocarbon solvent is ethylbenzene, benzene or toluene.

6. The solution as claimed in claim 4 or 5 wherein the solution is at a temperature from 80° C. to 130° C.

* * * * *